(12) United States Patent
Hasan et al.

(10) Patent No.: US 8,131,563 B2
(45) Date of Patent: *Mar. 6, 2012

(54) METHOD AND SYSTEM FOR GENERATING PERSONAL/INDIVIDUAL HEALTH RECORDS

(75) Inventors: Malik M. Hasan, Las Vegas, NV (US); John C. Peterson, Tucson, AZ (US); J. Dominic Wallen, Tucson, AZ (US)

(73) Assignee: HealthTrio LLC, Centennial, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/762,673

(22) Filed: Apr. 19, 2010

(65) Prior Publication Data

US 2010/0198623 A1 Aug. 5, 2010

Related U.S. Application Data

(63) Continuation of application No. 11/928,305, filed on Oct. 30, 2007, now Pat. No. 7,707,047, which is a continuation of application No. 11/495,093, filed on Jul. 28, 2006, now Pat. No. 7,440,904, which is a continuation-in-part of application No. 11/495,092, filed on Jul. 28, 2006, now Pat. No. 7,533,030, which is a continuation-in-part of application No. 11/495,135, filed on Jul. 28, 2006, now Pat. No. 7,509,264, which is a continuation-in-part of application No. 11/494,940, filed on Jul. 28, 2006, now Pat. No. 7,428,494, which is a continuation-in-part of application No. 11/494,933, filed on Jul. 28, 2006, now Pat. No. 7,475,020, which is a continuation-in-part of application No. 10/381,158, filed as application No. PCT/US01/42618 on Oct. 11, 2001, now Pat. No. 7,720,691.

(60) Provisional application No. 60/704,309, filed on Aug. 1, 2005, provisional application No. 60/239,860, filed on Oct. 11, 2000.

(51) Int. Cl.
*G06Q 10/00* (2006.01)
*G06Q 50/00* (2006.01)

(52) U.S. Cl. ............................................... 705/2; 705/3

(58) Field of Classification Search .................. 705/2, 3
See application file for complete search history.

(56) References Cited

U.S. PATENT DOCUMENTS 5,359,509 A  10/1994  Little et al.
5,517,405 A   5/1996  McAndrew et al.
(Continued)

FOREIGN PATENT DOCUMENTS

WO   WO 03/036542 A2   5/2003

OTHER PUBLICATIONS

Wang et al., "Implementing Patient Access to Electronic Health Records Under HIPAA: Lessons Learned," Perspectives in Health Information Management 1;11 Winter 2004.*

(Continued)

*Primary Examiner* — Neal Sereboff
(74) *Attorney, Agent, or Firm* — Barnes & Thornburg LLP

(57) ABSTRACT

A system and method for generating and/or updating a personal/individual health record. Inputs of data to the system may come from diverse sources including, but not limited to, patient questionnaires, insurance company (or other payor) claims data, hospitals, clinics and other institutional providers, and individual physicians and physicians' offices.

16 Claims, 10 Drawing Sheets

U.S. PATENT DOCUMENTS

| | | | | |
|---|---|---|---|---|
| 5,544,044 | A | | 8/1996 | Leatherman |
| 5,557,514 | A | * | 9/1996 | Seare et al. .................. 705/2 |
| 5,845,255 | A | * | 12/1998 | Mayaud ........................ 705/3 |
| 6,000,828 | A | * | 12/1999 | Leet .............................. 705/2 |
| 6,108,635 | A | | 8/2000 | Herren et al. |
| 6,112,183 | A | | 8/2000 | Swanson et al. |
| 6,151,581 | A | | 11/2000 | Kraftson et al. |
| 6,385,589 | B1 | * | 5/2002 | Trusheim et al. ............. 705/2 |
| 6,484,144 | B2 | * | 11/2002 | Martin et al. ................. 705/2 |
| 6,751,630 | B1 | * | 6/2004 | Franks et al. .................. 1/1 |
| 6,802,810 | B2 | | 10/2004 | Ciarniello et al. |
| 6,915,254 | B1 | | 7/2005 | Heinze |
| 6,988,075 | B1 | | 1/2006 | Hackerv |
| 2002/0138304 | A1 | * | 9/2002 | Fontanesi ..................... 705/2 |
| 2003/0212576 | A1 | | 11/2003 | Kim |
| 2004/0064343 | A1 | * | 4/2004 | Korpman et al. ............. 705/2 |
| 2005/0165623 | A1 | * | 7/2005 | Landi et al. .................. 705/2 |
| 2005/0234740 | A1 | * | 10/2005 | Krishnan et al. .............. 705/2 |

OTHER PUBLICATIONS

Wang et al., "Implementing Patient Access to Electronic Health Records under HIPAA: Lessons Learned" Perspectives in Health Information Management 1;11, Winter 2004.*

Supplementary European Search Report; Application No. EP 06 80 0539;Oct. 13, 2010; (all material itemized in this IDS).

Ledbetter, C.S. et al.: "Toward best practice: leveraging the electronic patient record as a clinical data warehouse." Journal of Healthcare Information Management: JHIM Summer 2001 LNKD-PUBMED: 11452574, vol. 15, No. 2, Jul. 2001.

"HealthTrio integrates SNOMED RT into web-based clinical communication platform" Virtual Medical World; Dec. 5, 2001, pp. 1-2; XP002603557.

* cited by examiner

| # | Organization | Information System | Ann's Information | System Identifier | MPI Identifier |
|---|---|---|---|---|---|
| 1 | Brightbed Hospital | Cerner HIS | Name: Ann Smith DOB: 2/10/1966 | AS12345 | 3243524354523 |
| 2 | Brightneedle Labs | Misys LIS | Name: Ann Smith DOB: 2/10/1966 | ANNSMI453 | 3243524354523 |
| 3 | Brightbill Pharmacy | Homegrown IS | Name: Ann Smith DOB: 2/10/1966 | 727-72-2772 | 3243524354523 |
| 4 | Brightclaim Health Plan | Amisys Claim Processing System | Name: Ann Smith DOB: 2/10/1966 | BC657483301 | 3243524354523 |
| 5 | Brightgolf Family Care | Millbrook Practice Manager | Name: Ann Smith DOB: 2/10/1966 | AnnSmithe | 3243524354523 |
| 6 | Bright Stuff Health Network | EPIC Practice Management | Name: Ann Smith DOB: 2/10/1966 | K6465737-01 | 3243524354523 |

Fig. 3

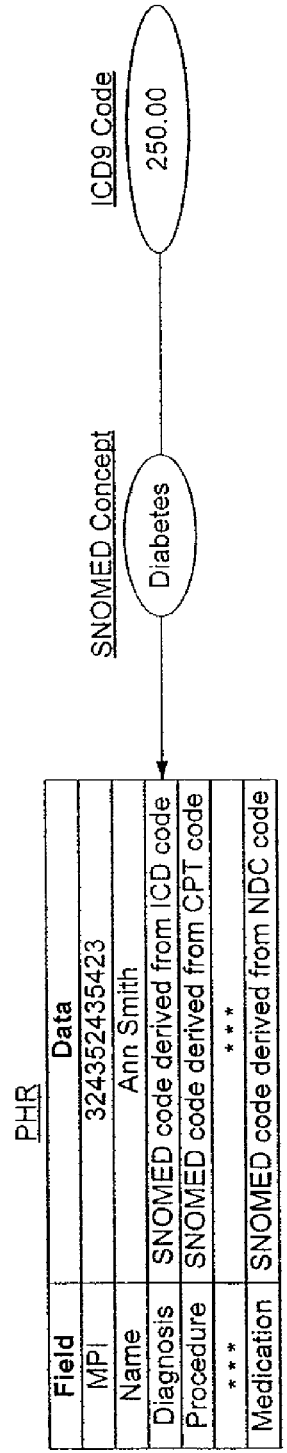

Fig. 5

| Consent | Clinical Permissions | Family Permissions |

Return to Previous Page

Permissions Information

Allbetter, Doctor

Protected Data Classes

These are special categories of data that require patient permissions to access

| Grant | Revoke | Action | Description |
|---|---|---|---|
| ○ | ● | Reproductive Health | On-line access to data related to reproductive health |
| ● | ○ | Mental Health | On-line access to data related to psychological behavior |
| ○ | ● | HIV | On-line access to data related to HIV |
| ○ | ● | Genetic Testing | On-line access to data related to genetic testing |
| ○ | ● | Abortion | On-line access to data related to abortion |
| ○ | ● | Sexually Transmitted Diseases | On-line access to data related to sexually transmitted diseases |

Functional Areas

| Grant | Revoke | Data Group | Description |
|---|---|---|---|
| ○ | ● | Visit Summary | Access your on-line visit summary |
| ○ | ● | My Plan for Health | Access to your on-line my plan for health |
| ○ | ● | Referrals & Authorizations | Access to your referrals and authorizations |
| ○ | ● | Medication Profile | Access your on-line medication profile |
| ○ | ● | Medical History | Access your on-line medical history |

[ Save ]   [ Cancel ]

Fig. 6

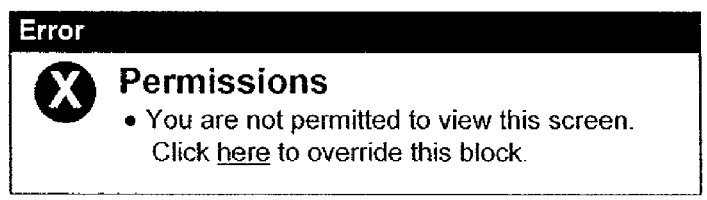

Fig. 7

| Override Restrictions | |
|---|---|
| User Information | |
| User ID | 1013 |
| User Name | Doctor Allbetter |
| Transaction Date/Time | 05-Jul-05 |
| • Reason | -Select- ▼ |
| | -or- |
| • Indicates Required Field | Other: |
| Note: | |

[ Continue ]  [ Cancel ]

Fig. 8

| Audit Permissions Report (reporting period April 20, 2006 – April 22, 2006) | | | | |
|---|---|---|---|---|
| Date/Time | User Name Role Access List | Member Name Member ID | Permission Type | Reason |
| 04-20-06 13:02:00 | Doctor Allbetter Provider Office H Specialist1 | Ann Smith 324352435423 | Consent | To provide routine care and treatment |
| 04-20-06 13:31:05 | Doctor Allbetter Provider Office H Specialist1 | Ann Smith 324352435423 | (FA) My Plan For Health | To provide emergency care |
| 04-20-06 13:52:10 | Doctor Allbetter Provider Office H Specialist1 | Ann Smith 324352435423 | (PDC) HIV | To provide emergency care |
| 04-20-06 14:10:22 | Doctor Allbetter Provider Office H Specialist1 | Ann Smith 324352435423 | (FA) Medication Profile | To provide emergency care |

[ Print ]  [ Close ]

Fig. 9

METHOD AND SYSTEM FOR GENERATING PERSONAL/INDIVIDUAL HEALTH RECORDS

RELATED APPLICATIONS

This application is a continuation of U.S. application Ser. No. 11/928,305, filed Oct. 30, 2007 now U.S. Pat. No. 7,707,047, which was a continuation of U.S. application Ser. No. 11/495,093 now U.S. Pat. No. 7,440,904, U.S. Ser. No. 11/495,092 now U.S. Pat. No. 7,533,030, U.S. Ser. No. 11/495,135 now U.S. Pat. No. 7,509,264, U.S. Ser. No. 11/494,940 now U.S. Pat. No. 7,428,494, and U.S. Ser. No. 11/494,933 now U.S. Pat. No. 7,475,020, all filed on Jul. 28, 2006. Each of these applications claimed priority to U.S. Provisional Application Ser. No. 60/704,309 filed Aug. 1, 2005, and are continuation-in-part applications of U.S. application Ser. No. 10/381,158, filed on Oct. 6, 2003 now U.S. Pat. No. 7,720,691, which was the National Stage of International Application No. PCT/US01/42618, filed Oct. 11, 2001, which claimed the benefit of Provisional Application No. 60/239,860 filed on Oct. 11, 2000. These applications are hereby incorporated by reference in their entireties.

FIELD OF THE INVENTION

This invention relates generally to computer methods and systems and, more particularly, to computer methods and systems for generating personal/individual health records for individuals by accessing and compiling data from diverse sources. In one embodiment, a system/method extracts and compiles data from, among other sources, payor claims data to generate a personal/individual health record for an individual.

BACKGROUND AND SUMMARY OF THE INVENTION

There is a substantial distinction between an electronic medical record ("EMR") and a personal health record ("PHR"), which is also commonly called an individual health record ("IHR"). The terms "PHR" and "IHR" are interchangeably used herein.

An EMR is provider-centric while a PHR is patient-centric. An EMR is not a complete health record of a patient, but is limited in scope to a specific health care provider. Notably, the electronic medical record does not contain any information from any other health care provider who does not have access or share the same specific EMR.

Electronic medical records are known. Typically, the EMR is established by hospitals or a group of physicians or less commonly by a physician. The EMR details each encounter between the patient and the provider for each episode of illness treated by the specific provider (hospital, physicians, or other care givers). Although the EMR is the commonly looked to as the medico legal record of that particular episode of illness and its management, it does not contain any information from any other provider who does not have access or share the same specific EMR.

A patient has no control over his/her EMR. For example, patients have no direct online access to their EMR and cannot make any entries in the record. Patients have no control over the access to their EMR and anyone who has access to the EMR of the specific hospital or physician group could access their health records. There is no complete global unified record of a patient in an EMR unless and until the entire healthcare is being delivered by the one provider group who is using the specific EMR for all patient encounters. The EMR system usually is used by a limited number of users (providers).

U.S. patents and published patent applications which relate to the topic of electronic medical records include: U.S. Pat. Nos. 5,867,821; 6,684,276; 6,775,670; 2004/0078227; and 2004/0172307. This listing of U.S. patent publications is not offered or intended to be taken as exhaustive, but rather as illustrative of patent filings on this topic. To the extent necessary for a complete understanding of the background relating to known electronic medical records and related systems, the disclosures of these publications are hereby expressly incorporated into this application by this reference thereto.

The present invention is not merely a system for electronically storing and accessing medical records, but relates to computerized systems and methods, including software attendant thereto, for generating a personal health record ("PHR"), also described as an Individual Health Record or Electronic Health Record (hereafter "IHR" or "EHR"). In contrast to an EMR, the PHR contemplated herein is intended to include all relevant health-related information for a patient, regardless of the specific health care provider. The clinical information regarding the individual patient may be collected from diverse sources including, but not limited to information from claims through the health plans, multiple EMR's being used from different providers providing care to that patient, medication records from the pharmacy benefit managers ("PBMs"), information from labs and imaging centers, and direct input by the patient to provide a unified personal/individual health record. The PHR may contain health records of millions of patients with online access to those millions of patients.

In one embodiment, the invention provides a system and method for generating a personal/individual health record that is compiled from diverse sources, such as patient questionnaires or direct input, health plans, pharmacy benefits managers ("PBMs"), labs, imaging centers, freestanding outpatient facilities, hospitals and physicians. The data collected from the diverse sources is organized into an individual health record for a patient. The individual health record may be integrated with SNOMED codes to allow that data to be encoded under specific medical diagnostic concepts. SNOMED is a division of the College of American Pathologists ("CAP"). SNOMED Clinical Terms ("SNOMED CT") is a scientifically-validated, clinical health care terminology and infrastructure. Health data can be captured, shared and aggregated in a consistent manner by the SNOMED CT terminology. The terminology currently contains over 350,000 hierarchically specified health care concepts, each with unique meanings and logic-based definitions. Additionally, these health care concepts have distinct relationships that support reliability and consistency for data retrieval. As used herein, the term "universal health care concept codes" means a common language that enables a consistent way of indexing, storing, retrieving and aggregating clinical data across specialties and sites of medical care. Each "universal health care concept code" is a unique identifier indicative of a node in a hierarchy of health care concepts to which other types of medical data can be mapped. The term "universal health care concept code" is intended to be synonymous with the term "SNOMED code."

In some embodiments, security and medical privacy could be provided such that a patient could have the ability to permit the entire individual health record to be viewed by designated persons or only permit selected parts of the record to be viewed by the authorized persons. This authorization is based on the ability of a patient to block any information relating to a protected class (e.g., mental health, reproductive system conditions in a female or STD, etc.) and/or functional area (e.g., illness/condition list, procedure list, medication profile, etc.). Any part of the record relating to that protected class and/or functional-area could be blocked and continued to be automatically blocked until a change is made by the patient.

According to another aspect, the invention provides a method for generating a personal/individual health record. The method may include the act of receiving a data element indicative of a health related parameter for a patient. The act of determining a SNOMED code corresponding to the data element may be included in the method. An entry may be inserted into a personal/individual health record associated with the patient based on the determined SNOMED code.

In some illustrative embodiments, the data element may include payor claims data. For example, the data element may be a health insurance claim code. Depending on the exigencies of a particular application, the data element may include patient questionnaires or direct input, health plans, pharmacy benefits managers ("PBMs"), labs, imaging centers, freestanding outpatient facilities, hospitals and physicians. Embodiments are also contemplated in which the data element may include an ICD code, a CPT code, a NDC code, LOINC code, or a code from a proprietary coding system, such as Lapcorps' lab and order codes.

The method may include the act of transmitting a description of the entry to a client system in some embodiments. In some cases, a first description and a second description may be associated with the entry. In such embodiments, the first description could be synonymous with the second description. For example, the first description may use medical terminology whereas the second description could use layman's terms. Preferably, the first description is transmitted if the client system is associated with a healthcare provider whereas the second description is transmitted if the client system is not associated with a health care provider.

In some illustrative embodiments, the method may include the act of determining whether the individual health record includes any entries related to the new entry. Preferably, any entries in the individual health record that are related to the entry are associated based on the determined SNOMED code.

According to another aspect, the invention provides a data processing system with a messaging facility configured to receive a data element indicative of a health related parameter for a patient. The system may include a correlation module configured to determine a SNOMED code corresponding to the data element. A PHR population engine may be operably associated with the correlation module, such that the PHR population engine is configured to insert health related data associated with the SNOMED code into a personal/individual health record associated with the patient.

In some embodiments, the system may include an access management module configured to communicate with a client system. In some cases, the access management module could be configured to transmit a description of the health related data to the client system. For example, the PHR population engine may associate more than one synonymous description with the health related data. Embodiments are contemplated in which some of the descriptions use medical terminology and others use layman's terms.

The system may include a filtering module in some embodiments. Typically, the filtering module may be configured to determine whether the client system is associated with a healthcare provider. The description transmitted to the client system may differ depending on whether the client system is associated with a healthcare provider. In some embodiments, the filtering module may be configured to change the description of the health related data based on a description of a SNOMED code up a SNOMED hierarchy to adjust the resolution of data.

In some embodiments, the system may include a PHR database configured to store a plurality of individual health records. The system may also include a data analysis module configured to identify patterns or relationships among the plurality of individual health records in the PHR database based on related SNOMED codes. For example, the data analysis module may be configured to measure effectiveness of healthcare treatment based on outcomes associated with the plurality of individual health records having related SNOMED codes. In some cases, the data analysis module may be configured to perform population studies based on SNOMED codes in the plurality of individual health records.

Embodiments are also contemplated in which the data analysis module may be configured to analyze a health care provider's quality of care and cost. For example, the data analysis module may profile health care providers based on patient outcomes associated with the health care providers. Likewise, the health care providers could be profiled in terms of costs, such as the cost charged by health care providers for various procedures. Health care providers could thus be ranked based on quality of care and cost. This information could allow various payors, such as insurance companies or governmental entities, to establish a list of preferred health care providers based on a formula that includes objective measures for quality of care and cost, as well as possibly other factors.

According to a further aspect, the invention provides a method of generating a personal/individual health record. The method may include the act of receiving a claims data element indicative of a health insurance claim associated with a patient. The SNOMED code corresponding to the claims data element may be determined. The method may also include inserting the SNOMED code into a personal/individual health record associated with the patient.

In some embodiments, the method may include the act of receiving a questionnaire data element indicative of an answer to a questionnaire by the patient. A SNOMED code corresponding to the questionnaire data element may be determined and inserted into the individual health record associated with the patient. Embodiments are also contemplated in which the method includes the act of receiving a clinical data element indicative of clinical data associated with the patient. In such embodiments, a SNOMED code corresponding to the clinical data element may be determined and inserted into the individual health record associated with the patient.

According to another aspect, the invention provides a method for generating a personal/individual health record. The method may include the act of receiving a data element indicative of a health related parameter for a patient. A health related concept that corresponds to the data element may be identified, such that the health related concept is selected from a hierarchical arrangement of health related concepts. A new entry may be inserting into the individual health care record that is representative of the identified health related concept. Also, the new entry may be associated with entries in the individual health record that have a hierarchical relationship to the new entry.

In some embodiments, the hierarchical arrangement includes nodes representative of medical diagnoses or medical procedures. For example, the hierarchical arrangement may include at least 300,000 nodes, such as a plurality of SNOMED Clinical Terms.

According to a further aspect, the invention provides a computer-readable medium having a data structure stored thereon. The data structure may include a diagnosis data field for storing a plurality of diagnosis data elements representative of medical diagnoses associated with a patient. For example, at least one diagnosis data element may be derived from a payor diagnosis code based on a SNOMED code. A procedure data field for storing a plurality of procedure data elements representative of medical procedures associated with the patient may also be included in the data structure. Preferably, at least one procedure data element is derived from a payor procedure code based on a SNOMED code. In some cases, the data element may be manually entered.

In some embodiments, a diagnosis data element may be derived from an ICD code. Embodiments are also contemplated in which a procedure data element may be derived from a CPT code. Other embodiments are contemplated in which other health-related information could be derived from other types of codes, such as LOINC codes or proprietary codes, such as Lapcorbs' lab and order codes.

Depending on the particular application, the data structure may include a medication data field for storing a plurality of medication data elements representative of medications associated with the patient. For example, a medication data element may be derived from a health insurance medication code based on a SNOMED code. In some cases, a medication data element may be derived from a NDC code. In some embodiments, the procedure data element may be derived from a questionnaire answered by the patient based on a SNOMED code associated with an answer to the questionnaire.

A still further aspect of the invention is achieved by a computer-usable medium having computer readable instructions stored thereon for execution by a processor to perform a method. In some cases, the method includes the act of receiving a claims data element indicative of a health insurance claim associated with a patient. A SNOMED code corresponding to the claims data element may be determined and inserted into a personal/individual health record associated with the patient. The method may include the act of receiving a questionnaire data element indicative of an answer to a questionnaire by the patient. The SNOMED code corresponding to the questionnaire data element may be determined and inserted into the individual health record associated with the patient. The method may include the act of receiving a clinical data element indicative of clinical data associated with the patient. The SNOMED code corresponding to the clinical data element may be determined and inserted into the individual health record associated with the patient.

According to another aspect, the invention provides a method for selectively restricting access to a personal/individual health record. The method may include associating an access list for each user capable of accessing a personal/individual health record associated with a patient, such that the access list categorizes the individual health record into a restricted set of data elements and an accessible set of data elements. A request may be received from a user for a data element in the individual health record. The method may include the act of determining whether the data element is in the restricted set of data elements by reviewing an access list associated with the user. If the data element is in the restricted set of data elements, access to the data element will be denied. However, if the data element is in the accessible set of data elements, the user will be allowed to access to the data element. In some embodiments, a predetermined list of possible restricted areas may be presented to a patient. The access list may be created responsive to selections by the patient.

According to a further aspect, the invention provides a method for generating a individual health record, in which the desired information from each source is pre-selected so as to collect information which is important and necessary for the continuing care of a patient and thus avoid massive accumulation of data in the patient's individual health record, which has none or little relevance to continuing care. This allows the user not to spend excessive amounts of time scrolling through lots of data to find actionable information. For example, a massive amount of information is typically collected in an EMR following an inpatient admission, such as extensive nursing reports, voluminous lab results, information regarding the scheduling of tests and procedures during the hospitalization. In some cases, the information which is imported in the PHR may be less than ten percent of the EMR and include only pre-selected types of data, such as the admission history and physical exam, discharge summary and discharge plans, and surgical report and pre-selected test results such as MRI, CT-Scans, and angiography results.

A further aspect of the invention is achieved by a method for generating a personal/individual health record. The method may include the act of receiving payor claims data associated with a patient. Encounter data indicative of an encounter between the patient and a health care provider may be derived from the payor claims data. A new entry may be inserted into a personal/individual health record associated with the patient based on the encounter data. In some embodiments, the deriving step may include deriving a primary care physician encounter history, an outpatient encounter history and a hospital admissions history from the payor claims data.

According to another aspect, the invention provides a method of filtering data in a personal/individual health record. The method may include receiving a request from a health care provider for a personal/individual health record associated with a patient. A specialty associated with the health care provider may be identified. The data elements in the individual health record that relate to the specialty of the health care provider may be determined. In response to the request, the health care provider may be presented with any data elements in the individual health record that were determined to relate to the specialty.

Additional features and advantages of this invention will become apparent to those skilled in the art upon consideration of the following detailed description of the illustrated embodiment exemplifying the best mode of carrying out the invention as presently perceived.

BRIEF DESCRIPTION OF THE DRAWINGS

FIG. 3 shows an example table using a MPI identifier according to an embodiment of the present invention;

FIG. 5 shows a block diagram of a portion of an embodiment of the present invention;

FIG. 6 shows an example window in which access control for the individual health record may be established;

FIG. 7 shows an example window denying permission to access a portion of the individual health record;

FIG. 8 shows an example window in which a user may override a restriction to a personal/individual health record;

FIG. 9 shows an example audit report that may be generated by the system according to an embodiment of the present invention.

DETAILED DESCRIPTION OF THE DRAWINGS

Figure 1:
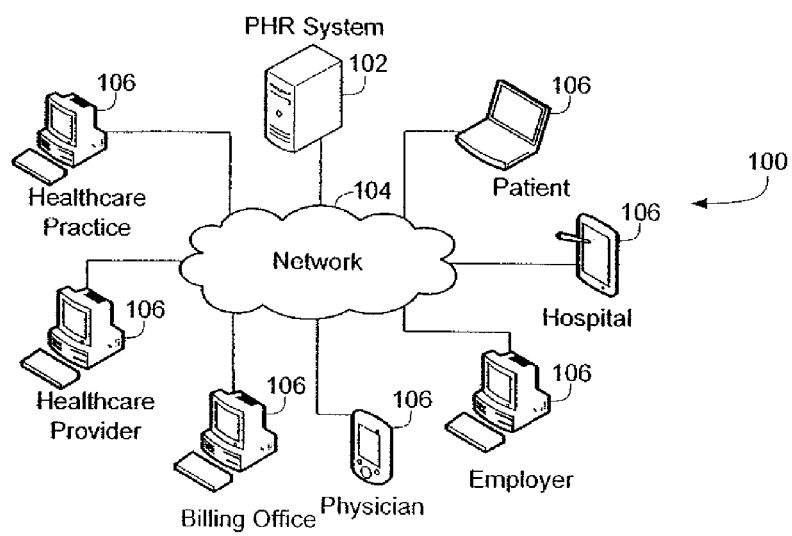
FIG. 1 shows a diagrammatic representation of a health care data system according to an embodiment of the present invention.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the disclosure.

As should be appreciated by one of skill in the art, the present invention may be embodied in many different forms, such as one or more devices, methods, data processing systems or program products. Accordingly, embodiments of the invention may take the form of an entirely software embodiment or an embodiment combining hardware and software aspects. Furthermore, embodiments of the invention may take the form of a computer program product on a computer-readable storage medium having computer-readable program code embodied in the storage medium. Any suitable storage medium may be utilized including read-only memory ("ROM"), RAM, DRAM, SDRAM, hard disks, CD-ROMs, DVD-ROMs, any optical storage device, and any magnetic storage device.

FIG. 1 shows a health care data system 100 in accordance with one illustrative embodiment that may be used to build, access, analyze, and/or update a Personal Health Record, also described as an Electronic Health Record or Individual Health Record (hereafter the terms "PHR" and "EHR" and "IHR" are intended to convey the same meaning). As shown, the health care data system 100 includes a personal health record system 102 ("PHR System") that is configured to provide access to individual health records via a network 104 to one or more client systems or users 106. The PHR system 102 may take the form of hardware, software, or may combine aspects of hardware and software. Although the PHR system 102 is represented by a single computing device in FIG. 1 for purposes of example, the operation of the PHR system 102 may be distributed among a plurality of computing devices. For example, it should be appreciated that various subsystems (or portions of subsystems) of the PHR system 102 may operate on different computing devices. In some such embodiments, the various subsystems of the PHR system 102 may communicate over the network 104.

The network 104 may be any type of communication scheme that allows computing devices to share and/or transfer data. For example, the network 104 may include fiber optic, wired, and/or wireless communication capability in any of a plurality of protocols, such as TCP/IP, Ethernet, WAP, IEEE 802.11, or any other protocol. Embodiments are contemplated in which the PHR system 102 may be accessible through a shared public infrastructure, such as the Internet. In such embodiments, any data transmitted over the shared public infrastructure is preferably encrypted, such as by using a public key infrastructure ("PKI") certificate and/or secure sockets layer ("SSL"). In some exemplary embodiments, a virtual private network ("VPN") may be used. Those skilled in the art should appreciate that various other security measures could be employed in relation to transmitting data over the network 104.

The client systems (or users) 106 may be any form of computing devices that can receive and send digital signals. By way of example, the client systems 106 may include personal computers ("PCs"), tablet computers, notebook computers, servers, personal digital assistants ("PDAs"), or cellular phones. The client system 106 shown in FIG. 1 includes labels indicative of typical users of the PHR system 102. For example, embodiments are contemplated in which patients, hospitals, employers, physicians, billing offices, healthcare providers and/or healthcare practices may access the PHR system 102. However, the client system's labels shown in FIG. 1 are provided solely for purposes of example, but are not intended to limit the type of users or require particular users to connect to the PHR system 10.

Figure 2:
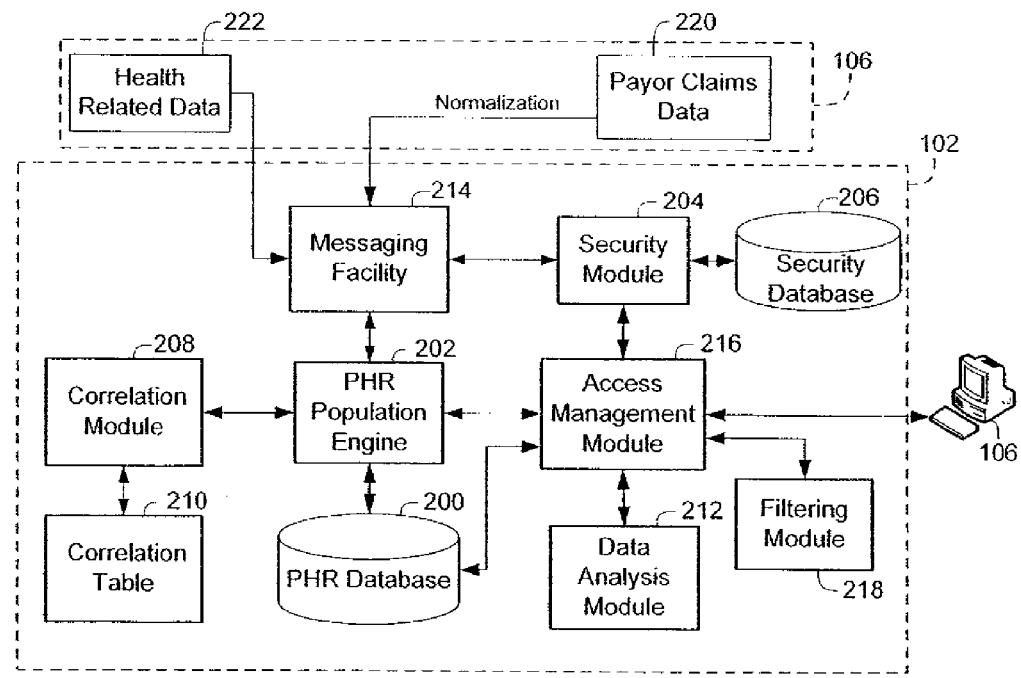
FIG. 2 shows a block diagram of an example PHR system according to an embodiment of the present invention.
Figure 4A:
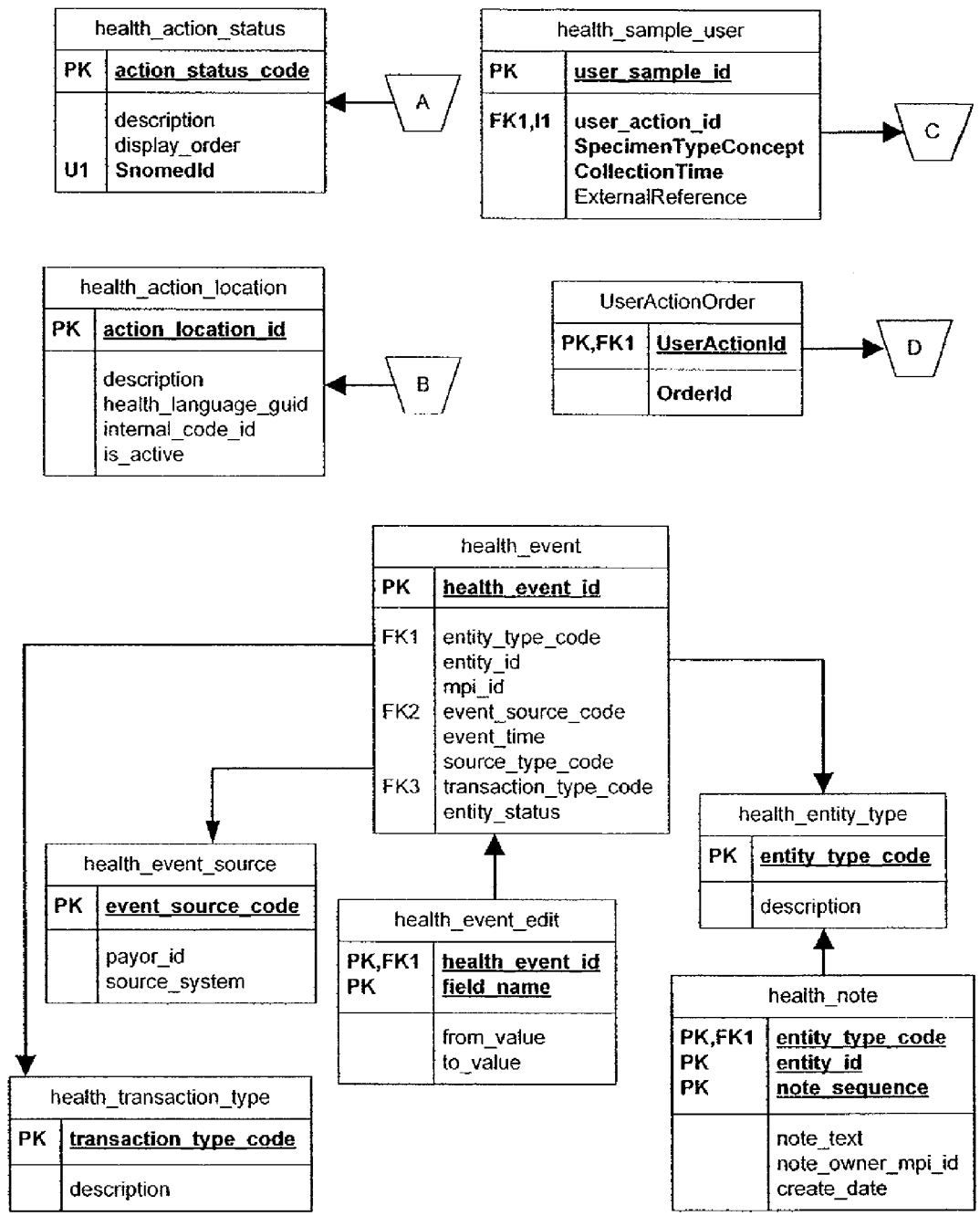
FIGS. 4A-4E show a database diagram illustrative of a portion of one embodiment of a system and method according to the present invention.
Figure 4B:
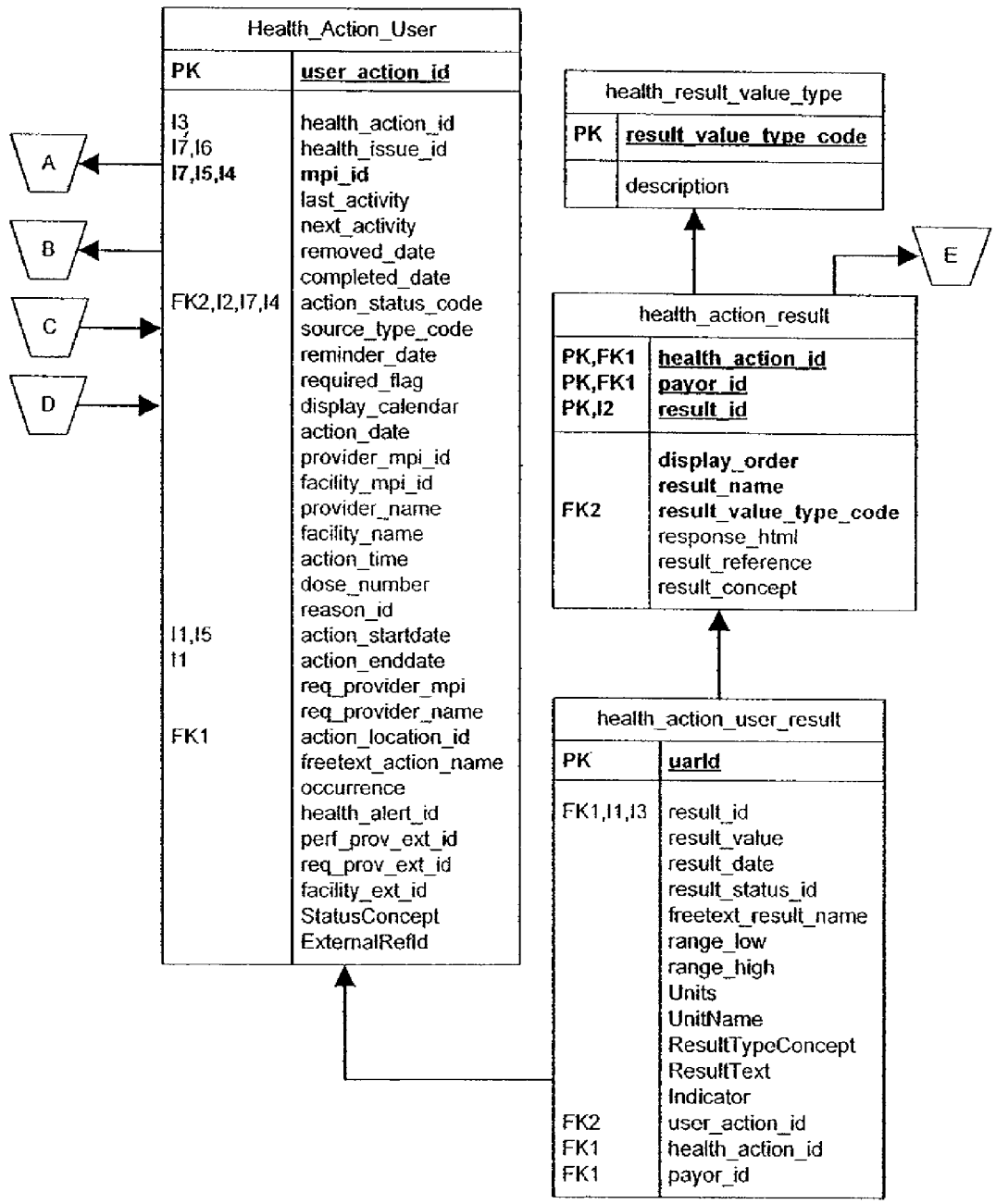
Figure 4C:
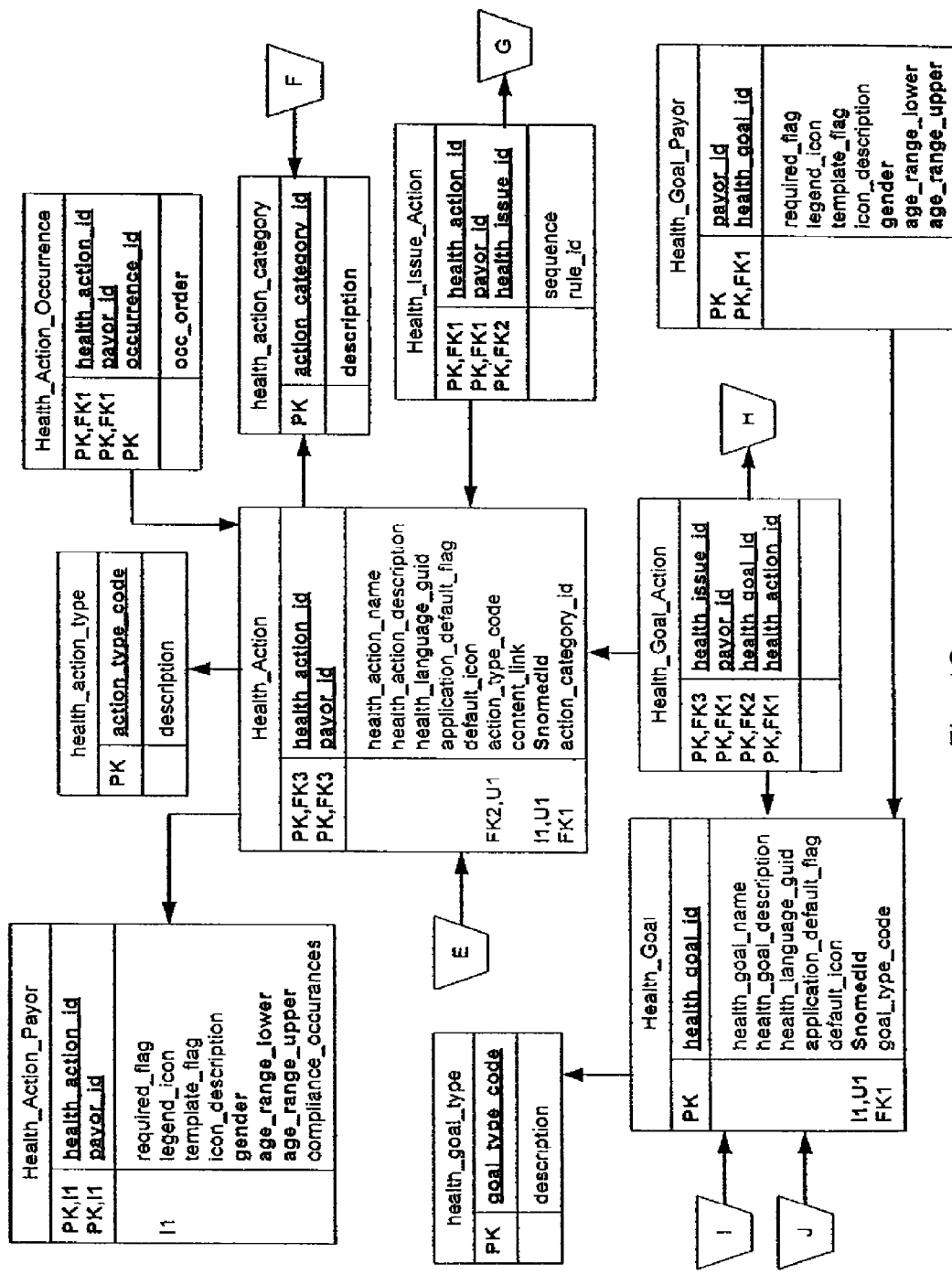
Figure 4D:
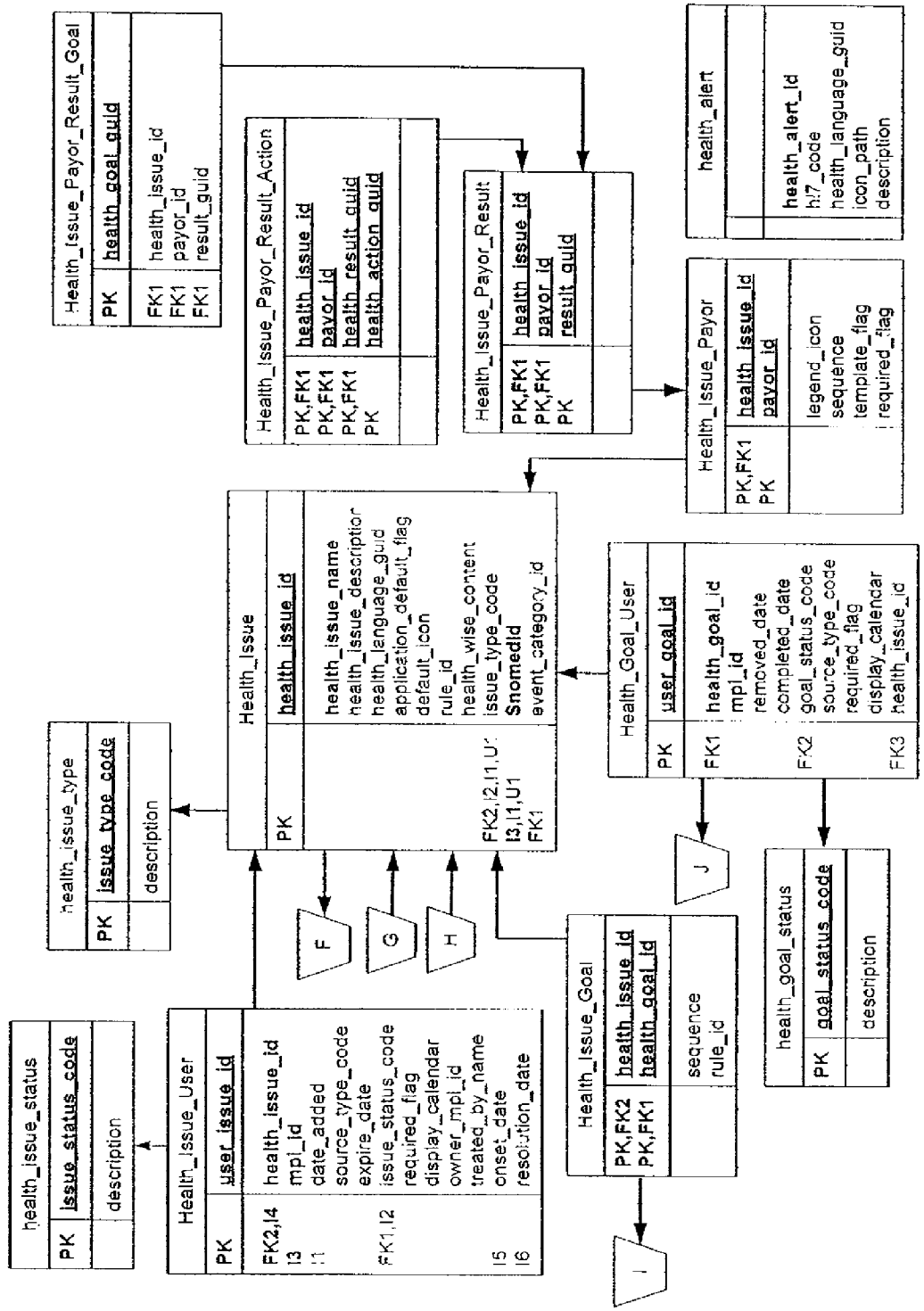
Figure 4E:
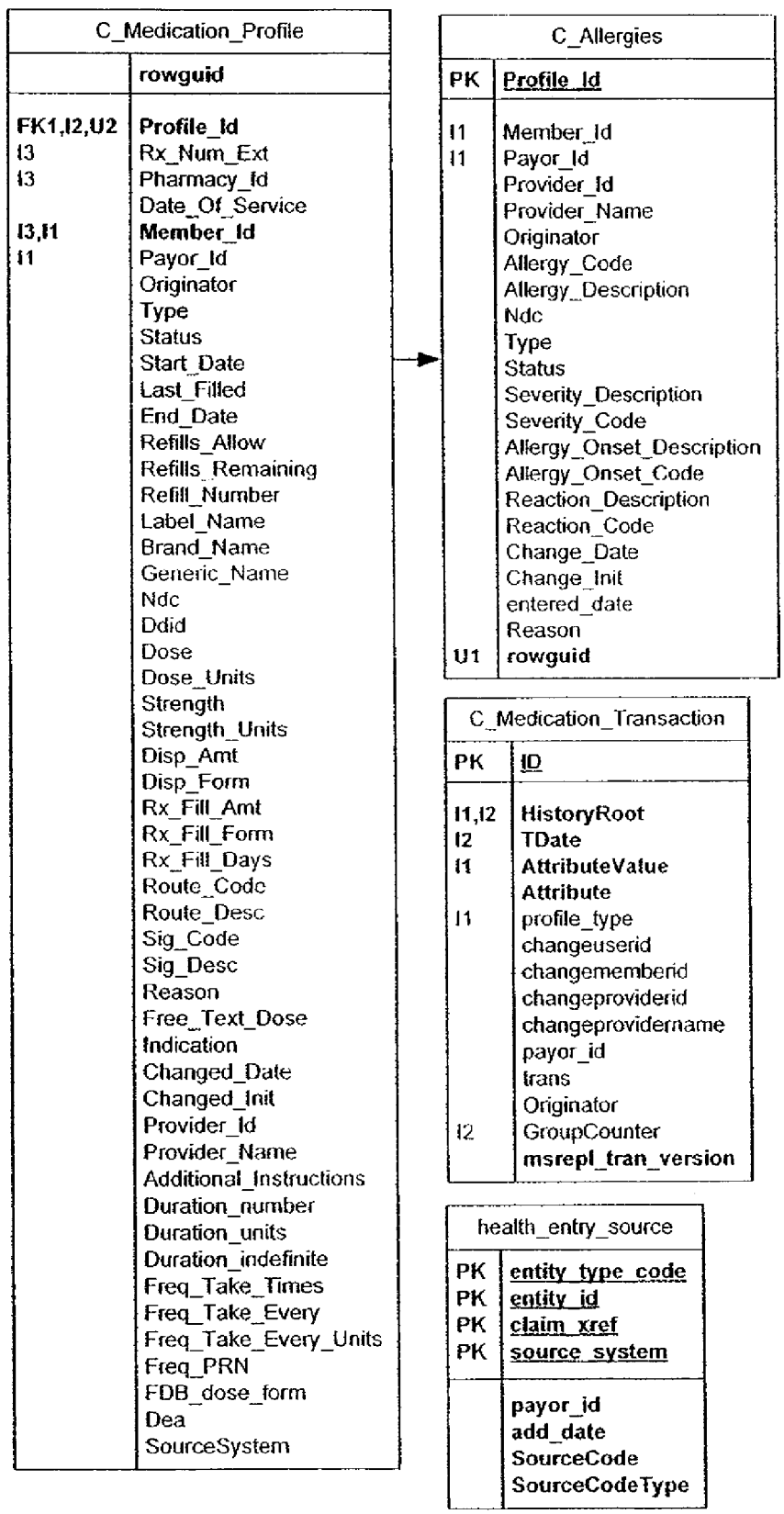

FIG. 2 shows an example embodiment of the PHR system 102. In the embodiment shown, the PHR system 102 includes a PHR database 200, a PHR population engine 202, a security module 204, a security database 206, a correlation module 208, a correlation table 210, a data analysis module 212, messaging facility 214, an access management module 216, and a filtering module 218. Embodiments are also contemplated in which one or more of these subsystems of the PHR system 102 are optional, but may merely be "nice to have" depending upon the exigencies of a particular situation. For example, the data analysis module 212 may be optional in some embodiments. By way of another example, the filtering module 218 may be optional in some embodiments. As shown, the PHR system 102 has access to payor claims data 220 and health related data 222. In some embodiments, the payor claims data 220 and the health related data 222 may be accessible to the PHR system 102 via the network 104 from the client systems 106.

The PHR database 200 may be structured to store various data relating to the health care of patients, including individual health records. Preferably, the PHR database 200 includes a plurality of PHRs for a plurality of patients. Typically, the PHR database 200 may include ten thousand to sixty million or more PHRs. Embodiments are contemplated in which the PHR database 200 may be a single database or a plurality of databases, each of which may be of any variety of database formats or languages. It should be appreciated that the PHR database 200 may be a logical dataset that may physically reside on a single storage medium or multiple storage media. In some cases, for example, the PHR database 200 may be a logical dataset that physically resides in multiple geographic locations.

In some embodiments, the PHR database 200 may include a master patient index ("MPI") field. The MPI field allows for the assignment of a unique identifier that defines an entity, such as a patient. Due to the massive amount of PHRs contemplated in the PHR database 200, many of the patients may have the same name. Consider, for example, a PHR database 200 that includes twenty million PHRs. In this example, there may be thousands of patients with the last name of "Smith" and numerous persons with the name "John Smith." Although the use of the MPI will differentiate the persons, the assignment of an MPI to a patient may include other criteria that may be unique to a patient. In some embodiments, for example, various other criteria, other than name, may be used to determine whether an entity has already been assigned an MPI, before an MPI is assigned. For example, the PHR system 102 may determine whether various data elements already exist in the PHR database 200 before assigning an MPI, including but not limited to tax IDs, birthdates, gender, address, etc. If the entity is determined to already exist, the information is applied to an existing PHR. Otherwise, a new PHR is created and a new MPI is assigned.

The MPI could be used to secure data, store patient specific settings, and/or act as a key when requesting health record data, for example. The MPI could also create a cross reference to identifiers already being used across different information systems of various health organizations. For example, hospitals, lab systems, provider offices, pharmacy benefits managers, health plans and/or other systems may be cross-referenced to the MPI, thereby tying all relevant data to an appropriate patient. By way of another example, the MPI allows a central patient search that would allow users to find patients across multiple, massive and discrete health related organizations without requiring a national ID number. In some organizations, for example, there may be data on fifteen million to twenty million patients. The use of the MPI also allows data collected from various sources to be aggregated into a single record {i.e., a single PHR with data collected from a plurality of sources}.

FIG. 3 is an example use of the MPI with respect to a patient identified as "Ann Smith." In this example, Ms. Smith has been treated by or visited the six listed healthcare organizations. Each of these organizations has assigned their own identifier for Ms. Smith shown by the system identifier column, while the MPI identifier remains a single unique tracking mechanism. In some embodiments, the MPI could not only generate a unique identifier for Ms. Smith, but could also cross reference information to the system identifier used by each of the organizations. In this manner, Ms. Smith's identification could be picked up when another message from the same system is received. This allows the matching of information originating from a wide range of medical sources and from multiple payors to a single comprehensive display about a patient. In some embodiments, the MPI could also be used to tie health information related to a patient and their family members. For example, the presentation of information regarding the patient and their family could be available in formats that assist both the health care provider and the patient in improving their health care.

FIGS. 4A-4D shows a diagram of an example relational database which could be used as the PHR database 200 in some illustrative embodiments. It should be appreciated that the database structure shown in FIG. 4 is for purposes of example only, but that a multiplicity of database structures could be used for the PHR database 200.

The PHR system 102 may include a PHR population engine 202 to populate and/or update the PHRs in the PHR database 200. The PHR population engine 202 may collect data from a wide variety of sources, such as medical claims, pharmacy claims, orders and results from laboratory systems, admission summaries, op report and discharge summaries from custom and standard hospital interfaces, and manually entered information from surveys, health risk assessments and direct entry. In some cases, manually entered data may be inputted by the patients themselves or representative from health plans, provider offices, hospitals, etc. By populating the PHRs from a variety of sources, the PHRs would not be limited to the data available from individual practices and hospitals. The table below shows a variety of sources from which the PHR may be populated, according to one embodiment, along with example information that may be gleaned from each source:

| SOURCE | METHOD OF COLLECTION |
| --- | --- |
| 1. Patients | Answers to questionnaires and surveys. Regular entries pertaining to management of their conditions, such as home blood glucose levels, airway test results, etc., to track the progress of the disease condition. Patients may also directly enter information, such as over the counter drugs, immunizations and allergies, into their PHR directly by connecting to the PHR system. |
| 2. Health Plans | Directly collecting the claims data from the claim processing systems on a periodic (e.g., daily basis) or real time basis. Deriving the data to obtain clinical information. This information may also be entered directly into PHRs by persons associated with the health plans, such as case and disease managers. |
| 3. Pharmacy Benefits Manager ("PBM") | Electronic tape or direct access to obtain data relating to prescriptions. |
| 4. Labs | From the lab systems using Universal interfaces (e.g. HL7) or customized interfaces. |
| 5. Imaging Centers | From the Imaging Center Systems using Universal (HL7) or customized interfaces. |
| 6. Freestanding Outpatient Facilities | From the EMR of the facility using Universal or customized interfaces. |
| 7. Hospitals | Information imported from the respective EMR's of the hospital using Universal Interfaces (such ass HL7) or customized interfaces. |
| 8. Physicians | a. From the claims submitted to the payers<br>b. direct online notes or input to the PHR |

Embodiments are contemplated in which the PHR population engine 202 may "pull" data from various sources. In some embodiments, for example, a "flag" or other notification could be sent to the PHR population engine 202 that health related data is ready to be updated. It should also be appreciated that various health related organizations could "push" data to the PHR population engine 202. For example, the client systems 106 may access the PHR system 102 to update the PHR of a patient in the PHR database 200. In other embodiments, the PHR population engine 202 may periodically receive data from various sources. For example, the PHR population engine 202 may download payor claims data (or other health related information) from an insurance company (or other payor or health provider) on a daily, weekly or other periodic basis. Embodiments are contemplated in which the PHR population engine 202 may download payor claims data or other health related data on a "real time" basis. The term "real time" does not necessarily mean instantaneous, but merely means that the PHR population engine 202 would update the PHR database 200 with new information before the information would be needed by a health care provider. For example, consider a patient that is referred to a specialist based on a visit with his/her primary care physician. In this example, the PHR population engine 202 would be considered to update the patient's PHR on a "real time" basis if the PHR is updated with information from the visit with the primary care physician prior to the visit with the specialist, whether the appointment with the specialist is scheduled the same day as the visit to the primary care physician, the next day, a week later, etc.

In some embodiments, the PHR system 102 may include a messaging facility 214 to interact with the PHR population engine 202 in handling messages that are received from various sources, such as client systems 106. In some cases, the messaging facility 214 may also generate response messages for client systems 106 that can programmically request an electronic copy of the PHR. Embodiments are contemplated in which programmical requests for portions of the PHR may be denied based on permissions associated with the PHR, as described below with respect to the security module 204.

Preferably, the messaging facility 214 is configured to handle messages 20 in a variety of different formats, both standardized formats, and custom formats. The message formats described herein are provided merely for purposes of example; however, it should be appreciated that the messaging facility 214 is not limited to the formats specifically described herein. By way of example, the messaging facility 214 may be capable of handling messages in HL7v2.4 and HL7v2.5 formats. These message formats include support for various health related information, such as hospital admission and discharge summaries, lab orders, radiology orders, radiology results and lab results. By way of another example, the messaging facility 214 may include support for HL7v3 format.

Embodiments are contemplated in which the messaging facility 214 includes support for ANSI-X12 837. This message format is defined by the American National Standards committee and imposed by the Health Insurance Portability and Accountability Act ("HIPAA") as the currently required standard for passing health care claims data between organizations. This message format includes a wealth of clinical information, including diagnosis and procedure codes, provider specialty data, treatment dates and many others.

The messaging facility 214 may also include support for NCPDP 5.1 format. This standard for passing prescription and medication information between entities was defined by the National Council for Prescription Drug Programs organization, and has been adopted by HIPAA as a pharmacy batch standard. While this message could be sourced from many locations, it would most likely be delivered from a Pharmacy Benefits Manager ("PBM"). The PBM may be within a health insurance plan, or operate as an individual entity, for example.

In some embodiments, the messaging facility 214 may receive messages over a secure connection to a web service. In some embodiments, the messaging facility 214 may include a certification mechanism to ensure that the organization is eligible to submit and request information from the PHR system 102. For example, each participating entity may be issued a Public Key Infrastructure ("PKI") certificate that will allow verification that only authentic messages are passed to the PHR system 102. The messages may be sent on a real-time basis from some organizations, typically hospitals and laboratories, but may be sent on a periodic basis from other organizations, such as health insurance plans and PBMs.

In some embodiments, the PHR population engine 202 may have access to payor claims data 220. The term "payor claims data" is intended to be broadly interpreted to include any patient related data associated with the payment of health related services. Typically, payor claims data 220 may be available from (or sent to) payors(s). As used herein, the terms "payor" and "payors" means health insurance plans and/or governmental bodies that pay for health related services, and/ or pharmacy benefit managers. For example, the payor claims data 220 may include, but are not limited to International Classification of Diseases ("ICD") codes, Current Procedural Terminology ("CPT") codes, National Drug Code ("NDC") codes, treating physicians, treatment dates, manually entered data, or other data formats. A wide variety of information may be obtained through the payor claims data 220. An illustrative example of information that could be collected for a PHR from the payor claims data 220 is provided below:

General Information
Age.
Sex.
Outpatient Encounter History
Vaccination history.
Mammography in women; retinal examinations for diabetics; colonoscopy for adults; PSA tests for males; etc.
Visits to primary care doctor. Dates, duration, frequency, main diagnosis at each visit, medication prescribed following each visit, tests ordered with each visit, changes of medication as a result of each visit, changes in the frequency of visits to the PCP, changing diagnoses following visits.
Referrals or orders for lab tests and imaging tests with the diagnosis justifying the tests. Subsequent visit history to specialists, further tests and admissions to hospitals.
Referrals and visits to specialists. Diagnoses by specialists, lab tests and imaging tests ordered by specialists and diagnoses justifying tests.
Medications prescribed by specialists, with diagnoses. Duration of medication.
Multiple same-condition specialists, or physicians for the same diagnoses.
Medication to medication alerts generated. Medication-clinical condition adverse reaction alerts generated.
Psychotherapy/Psychiatric Therapy—dates, name of caregiver, diagnoses, medication.
Hospital Outpatient Encounter History
Tests done at the out patient facility—dates, tests and diagnoses. Any repeats?
Out-patient surgery—date of surgery, type of surgery, diagnoses for surgery, name of surgeon, name of anesthesiologist, complications.
Hospitalizations following out-patient surgeries.
Physical therapy—dates, duration referring physician and diagnosis.
Out-patient or in-patient drug rehabilitation treatment—dates, treating physicians, diagnoses and follow up visits. Medication associated or linked with these therapies.
Urgent Care/ER Visits—dates, duration, names of physicians, names of facilities, tests run, and diagnoses.
Admissions to hospitals or physician referrals resulting from urgent care/ER visits. Medications prescribed and procedures performed.
Ambulances/medical transportation—dates, number of times called in a span of time, diagnoses, treatment rendered by EMT.
Hospital Admissions
Name of hospital. Date of admission. Date of discharge. Admitting diagnosis and discharge diagnosis. List of complications. L.O.S.
Problems list. The names/times seen by specialists, their specialists and diagnoses by them. Time spent by each physician on every visit. The diagnoses or conditions for which they were seeing the patient.
Tests—lab tests, biopsies, surgical specimen exam, imaging tests and other tests with the dates and diagnoses and names of referring physicians and reporting physicians.
Treatment days in regular units. Treatment days in intensive care.
Post Hospitalization Management: ECF, NH, physical therapy, at home nurse visits, and infusion therapy.
Medication following discharge.
Ongoing complications, if any.

Readmission and readmission diagnoses and dates, dates of admission and discharge, treating physicians and their specialists and the time they spent with the patients in the hospital.

It should be appreciated that the above list is provided for purposes of example only, but that additional information may be obtained from the payor claims data 220.

It might at first appear implausible that transactional information, such as payor claims data 220, would provide meaningful medical or clinical information for inclusion in a PHR. However, payor claims data 220 creates a type of virtual medical record. Every claim which is processed typically includes, in addition to various demographic information, procedural or visit codes and diagnostic codes. Payor claims data 220 is generally more comprehensive relating to the encounters between the patients and different as well as diverse providers than the electronic medical records kept by individual providers since a health plan (or other payor) will generally receive claims from all or most of the significant care providers for an individual. Using the electronic medical records of the individual providers to assemble a PHR would, at best, be much more difficult, and would likely result in a record that is lacking in a full list of encounters, especially providers whose access was not provided for whatever reason. Another advantage to using the payor claims data 220 is that this data is relatively precise and orderly when compared to other data sources in the health care industry. The payer claims data 220 also provides a structure which is useful in methodically organizing and populating the data, and prioritizing the manner in which extracted data is displayed. In addition, the payor claims data 220 would not need coordination from the creators/keepers of the data. For example, the use of payor claims data 220 to add information about the hospital admission of a patient would not need the coordination of the hospital.

Preferably, the payor claims data 220 is "normalized" or placed into a standard format by a separate process. One such process is the Connect™ process available from the assignee of the present application. This process is described in U.S. patent application Ser. No. 10/381,158 entitled "System for Communication of Health Care Data" filed on Mar. 21, 2003 and claiming the benefit of PCT International Application No. PCT/US01/42618 filed on Oct. 11, 2001. Both U.S. and PCT applications are hereby expressly incorporated into this application by this reference thereto. Although specific to the payor from whom the payor claims data is obtained, the payor claims data 220 may be more readily utilized by the remainder of the PHR system 102 than "raw" data available from various health related organizations.

In the embodiment shown, the PHR population engine 202 has access to other health related data 222, which could be used to supplement and/or enhance the payor claims data 220. For example, the health related data 222 may be collected from patients using questionnaires. By way of another example, the health related data 222 may include clinical data obtained from various entities, such as hospitals, labs, imaging centers, or outpatient surgery centers. In addition, the health related information 40 could be obtained from physicians and/or physician offices.

In some embodiments, for example, individuals may be asked to complete questionnaires at the time of enrollment into a health plan, or at some later time when a PHR is being developed. The following is an illustrative example of information collected for a PHR using questionnaires:

General Information
Race.
Weight.
Change in Weight.
Height.
Blood Pressure.
History of diabetes, asthma, stroke, heart attack and other conditions.
History of Accident: automobile, motorcycle, bicycle and work-related.
History of potentially dangerous hobbies.
Family history of overweight, high blood pressure, diabetes, heart disease, cancer.
Lifestyle factors: smoking, alcohol, drugs, exercise and sports.
Visits to various countries where a disease could be contracted.
Any other history information that can be obtained by changing the questions and adding further questions.
Outpatient History
Vaccination history.
Mammography in women; retinal examinations for diabetics colonoscopy for adults; PSA tests for males; etc.
Medications prescribed by specialists, with diagnoses. Duration of medication.

It should be appreciated that the above list is provided for purposes of example only, but that additional information may be obtained from patient questionnaires.

In some embodiments, the health related data 222 may include clinical data from hospitals, labs, imaging centers, outpatient surgery centers, and/or similar entities. In some cases, the clinical data may be extracted using a standard format. For example, this information is generally available in electronic form in Health Level Seven ("HL7") format and can be efficiently extracted through the use of interfaces designed for compatibility with this format. HL7 is a non-profit volunteer organization headquartered in Ann Arbor, Mich. that is an American National Standards Institute ("ANSI")-accredited Standards Developing Organization ("SDO") operating in the field of healthcare. This organization develops specifications that enable disparate healthcare applications to exchange key sets of clinical and administrative data. It should be appreciated that an interface may be provided to extract data from some other form or format. The following is an example list of clinical information that may be collected from the health related data 222:

Inpatient admission history and physical examination.
Inpatient discharge summary.
Selected lab results done during the hospital stay (some of the test results may be irrelevant for continuing care and may just add to the clutter).
Imaging test results.
Pathology reports, including reports of biopsies.
Medications administered to the patient.
Any other information which is considered relevant for continuing care.

It should be appreciated that the above list is provided for purposes of example only, but that additional clinical information may be obtained from various entities.

The manner in which such clinical information may be accessed will depend on the state of record keeping in each individual entity. In hospitals having relatively modern electronic medical record systems that use the HL7 format, for example, it should be relatively easy to gather the desired clinical information from the electronic medical record ("EMR") of each patient for each encounter. In hospitals without comprehensive EMR systems, or in those using different data formats, the information gathering may still take place, albeit through individually crafted interfaces or other means specific to the particular entities or data types. For example, lab, pathology reports and imaging tests results could be accessed by building interfaces specific to the systems used to maintain this data. The fact that many hospitals use outside vendors for such services, and an individual vendor may serve many hospitals, will allow an interface to be used across a number of providers. Similar solutions could be adopted with other types of clinical information. Relevant information may also be accessed through pharmacy systems, such as those maintained by hospitals or third parties. Admission history and physical examination and discharge summaries may also be accessed through transcription centers. This approach may be used with labs, imaging centers, outpatient surgery centers, and other entities. Many, if not most, of these entities have modern electronic systems, which are HL7 compatible, facilitating the gathering of relevant information. As discussed above, however, other techniques could be used to gather the information if not in HL7 format.

The health related data 222 may include information gathered from physicians and/or physician offices. There are thousands of physician-run clinical software systems in existence, with more variety and less standardization in record keeping than is the case with the other sources discussed above. One approach to obtaining information from physicians is to recognize what information is not available from payor claims data, questionnaire data and clinical data, and then focusing on obtaining that information. Typically, the information which this includes is relatively limited and consists mainly of results of some tests done in physician offices. Examples of such tests include EKG's, cardiac stress tests, echocardiogram tests, EEG's, EMG's, nerve conduction studies, and ultrasound tests done in physician offices. One possible approach to facilitate and incentivize physicians to provide this information to assist in building a patient's PHR is to ask or require providers to supply the information to a PHR portal. In some cases, for example, the supply of such information could be a condition for payment in connection with the subject tests.

In some embodiments, the PHR population engine 202 may interact with the correlation module 208 to correlate health related data 222 and/or payor claims data 220 with a health care concept in an arrangement of health care concepts. Preferably, the correlation module 208 encodes the health related data 222 and/or payor claims data 220 into SNOMED ("Systematic Nomenclature of Medicine") codes. The SNOMED codes or health related data based on the SNOMED codes may be inserted into the patient's PHR. In some embodiments, other health entries in the PHR relating to the SNOMED code could be associated in the PHR, regardless of the format or mechanism from which the information is derived. By using SNOMED codes in the PHR, differing types of entries, such as illness/conditions, procedures, care plans, biometric trackers, medication profile and lab results, could be tied together for better decision making, data analysis, application of permissions and enhanced health tracking.

SNOMED is a division of the College of American Pathologists ("CAP"). SNOMED Clinical Terms ("SNOMED CT") is a scientifically-validated, clinical health care terminology and infrastructure. Health data can be captured, shared and aggregated in a consistent manner by the SNOMED CT terminology. The terminology currently contains over 350,000 hierarchically specified health care concepts, each with unique meanings and logic-based definitions. Additionally, these health care concepts have distinct relationships that support reliability and consistency for data retrieval. In some embodiments, the correlation module 208 may be associated with a correlation table 210, which may map health related data 222 and/or payor claims data 220 into a health care concept, such as a SNOMED code.

FIG. 5 provides an example with a PHR for a patient identified as "Ann Smith." In this example, the PHR includes a MPI field, which contains the MPI associated with Ann Smith, as discussed above. The example PHR includes diagnosis, procedure, and medication fields in which the SNOMED codes derived from ICD codes, CPT codes and NDC codes, respectively, may be stored. In the example shown, the payor claims data 220 is the ICD9 code of 250.00. The correlation module 208 could correlate this ICD9 code into the diabetes concept. The PHR population engine 202 may include the SNOMED code associated with the diabetes concept into the diagnosis field of the PHR for Ann Smith. Other health entries in the PHR relating to diabetes could be associated with this entry in the PHR, regardless of the format or mechanism from which the information is derived, whether from an ICD code, a CPT code, a NDC number or manually entered data. Physicians, patients and others could then categorize information related to specific health concepts using the SNOMED codes, including visits, illness/conditions, procedures, immunizations, medications, health action plans, lab results or other related data. The use of the MPI field could further enhance the PHR system 102. Since the MPI identifies the patient and the SNOMED code designates the health concept, the PHR system 102 may collect and present diverse data in a PHR that can be organized, stored, viewed, and managed by all interested parties in health care transactions.

The PHR system 102 may include an access management module 216. The access management module may provide an interface to the PHR system 102 for client systems 106, to enhance and/or supplement the access provided by the messaging facility 214. In some embodiments, for example, the access management module 216 may provide a web-based portal to access PHRs in the PHR database 200.

In some embodiments, for example, a patient may access his/her PHR via the web-based portal (or through another connection to the PHR system 102). This would allow the patient to supplement his/her PHR with additional information, such as over the counter medications, allergies, immunizations, etc. The patient could also view his/her PHR using the access management module 216. For example, the patient could view a diagnosis, laboratory results and other information in his/her PHR via the web-based portion (or other connection). In some circumstances, the timing of patient access to certain records in the PHR may be controlled. For example, a physician may not want a patient to view the lab results until the physician has reviewed the lab results. Accordingly, in some embodiments, the access management module 216 may be configured to determine whether records in the PHR have been "released" for patient access. If not, the access management module 216 would not allow the patient to view any "unreleased" entries, but only allow access to "released" records.

In some embodiments, the access management module 216 may interact with a security module 204 that restricts access to PHRs in the PHR database 200. For example, some providers may not be granted access to portions of the patient's PHR that may be considered sensitive. Whenever a user accesses a patient's PHR, the security module 204 may evaluate whether permission has been granted to that user so that only the information contained in the PHR to which that user has been granted permission will be displayed. The use of the security module 204 in this manner allows a patient to completely control access to his/her PHR. For example, the patient may specify the default permissions for various types of entities, including his/her spouse, family members, primary care physicians, and other health care providers. The term "health care provider" is intended to be broadly construed to include any persons who provide health care as part of their job responsibilities. In some embodiments, the patient may specify the particular individuals to whom permissions may be granted. The use of permissions addresses privacy concerns of patients, which may allow a higher level of usage, as well as better care resulting from more patients sharing data electronically with their healthcare providers via the PHR.

In some embodiments, portions of the PHRs may be protected by the security module 204 based on the types of health information that a patient may consider sensitive. For example, a patient may elect to allow the designed physician to have full access to their various illness/condition list, while restricting access to selected diseases, such as sexually transmitted diseases or psychological disorders. If a portion of the PHR relates to an area that may be considered sensitive, the security module 204 may consider that area of the PHR to be a protected data class. For example, information in a PHR related to reproductive health, mental health, HIV, genetic testing, abortion, sexually transmitted diseases, alcohol abuse, drug abuse, AIDS, contraceptive issues, abuse or neglect, sexual assault and/or other sensitive health issues may be considered protected data classes. Embodiments are contemplated in which a predefined list of sensitive health issues could be considered protected data classes. Of course, it should be appreciated that additional data classes could be added and/or deleted from the list of protected data classes. In some embodiments, the correlation of payor claims data and/or health related data into SNOMED codes, as described herein, may be used to categorize the PHR into protected classes for restricting access to the PHR. For example, each SNOMED code related to HIV could be associated with the HIV protected class.

Embodiments are also contemplated in which the security module 204 may restrict access based on functional areas of a PHR. By way of example, function areas of a PHR may include summary, health risk assessment, health calendar, medical history, medication profile, visit summary, health event record, illness and conditions, my plan for health, account summary, benefits and eligibility, change PCP, claims, member information, referrals and authorizations, permissions.

The security module 204 may allow a patient to select entities that may access protected data classes and/or functional areas of his/her PHR. Embodiments are contemplated in which a patient may revoke consent, which would prevent electronic retrieval of his/her PHR. In some embodiments, a patient may restrict access to certain protected data classes and/or functional areas. It should be appreciated that there could be a variety of reasons for a patient to restrict access to protected data classes and/or functional areas. For example, a patient may not want clinician specialists to see information not related to their specialty, or may not want a spouse (or other family member) to view medication information. In some embodiments, the security module 204 may provide an error message if access to a restricted area is attempted. In some cases, the protected data classes and/or functional areas that have been restricted may not be displayed, which would prevent an entity being restricted from realizing that a restriction is in place. If a spouse of a patient reviewed his/her PHR, for example, the protected data classes from which the spouse was restricted may not be visible to the spouse; accordingly, the spouse would not know that a restriction to accessing the PHR was in place.

FIG. 6 shows an example interface that allows a patient to restrict access to portions of his/her PHR. In this example, the patient has selected the access rights for a healthcare provider called "Doctor Allbetter." As shown, the patient has revoked Doctor Allbetter's access to all protected data classes, except information related to mental health. In addition, the patient has revoked Dr. Allbetter's access to all functional areas, In some embodiments, default access rights to a PHR may be established. For example, a payor may define default access rights for each of its members. Embodiments are contemplated in which the default access rights could be based on various factors, such as relationship, gender, age and location of the patient. In this manner, a reasonable level of access rights based on the patient could be established, even before the patient customizes the access rights as discussed above.

Embodiments are contemplated in which the security module 204 may include role-based security. In such embodiments, the users may be assigned a role to define the portions of the PHRs to which the user has access. This eliminates the need to establish security access levels separately for each user. For example, each role may include a security profile defined by the organization that the data that would be accessed. By way of another example, heath plan data may be protected by the role that the health plan defines for the user, while the hospital data may be protected by a role that the hospital has defined.

In some embodiments, the security module 204 may permit a restriction to be overridden in certain circumstances. For example, this may allow a physician to view a restricted portion of a PHR for emergency care. By allowing some restrictions to be overridden in certain circumstances, this balances privacy concerns with the possible need for emergency care where PHR data is required due to the state of the patient.

As shown in FIG. 7, for example, a user may be presented with a window showing that permission has not been granted to the portion of the PHR for which access is sought, but that the restriction may be overridden. In this example, the word "here" in the window is a hyperlink that allows the user to override the restriction. It should be appreciated that FIG. 7 is provided for purposes of example, but that numerous different types of user interfaces could be used to allow a restriction to be overridden.

In some embodiments, the user may be required to provide a reason for overriding a restriction. For example, as shown in the illustrative embodiment in FIG. 8, the user may be allowed to select from a list of possible reasons for overriding the restriction and/or manually enter a reason. This reason, along with other information regarding the override, may be stored by the security module 204, as described herein with respect to auditing of the PHR.

The security module 204 may create an audit trail regarding access to a patient's PHR. For example, the audit may include when permission was granted, who was granted permission, who recorded the granting of the permission and what permissions were granted. In some embodiments, the security module 204 may audit whenever a user accesses a patient's PHR. For example, the audit may include when a patient's PHR is accessed, who accessed a patient's PHR and what portions of the PHR were accessed. In some embodiments, the audit and permission data may be stored in the security database 206 and/or in the PHR database and/or other storage location.

FIG. 9 shows an example audit report based on information gathered by the security module 204. In this example report, the user "Doctor Allbetter" has accessed the PHR of a patient called "Ann Smith" on four occasions. Each time that Doctor Allbetter accessed Ann Smith's PHR, the audit report notes the date and time that the PHR was accessed. For information in the PHR to which Doctor Allbetter had access, the example report includes a "permission type" column and a column with the reason for accessing the PHR. In this example, the first time Doctor Allbetter accessed the PHR, he/she had consent to access that portion of the PHR. In each of the other three occasions, Doctor Allbetter overrode the permissions to access a functional area (shown as "FA") and a protected data class (shown as "PDC") as part of emergency care.

In some embodiments, the PHR system 102 may include a data analysis module 212. The data analysis module 212 could be configured to identify patterns or relationships in data contained in the PHR database 200 for a single patient or across multiple patients. For example, the data analysis module 212 could perform population studies across many healthcare events, such as condition, progress of condition, impact of co-morbidities on the underlying condition, procedures and medications. Due to the plurality of PHRs in the PHR database 200, the data analysis module could analyze data relating to a large number of patients. The data analysis module 212 could provide an outcomes measurement. For example, the data analysis module 212 could identify the medications that were the most successful in controlling diabetes. By way of another example, the data analysis module 212 could compare the results of surgery versus medical treatment. By way of another example, the data analysis module 212 could analyze surveys in the PHR database 200 regarding the effectiveness of treatments, drugs, etc.

In embodiments in which SNOMED encoding is used, as described herein, the data analysis module 212 could use SNOMED codes as a mechanism to tie events together, to identify patterns or relationships. For example, the use of SNOMED codes in the PHR database 200 aids in outcomes measurements because healthcare events, such as conditions, procedures, medications, and survey information, could be tied to related SNOMED codes. By way of example, survey results covering the effectiveness of chiropractic care for back pain could be measured, as well as the effectiveness of wellness programs. The use of an MPI could also aid in data analysis. For example, the use of an MPI ensures that all episodes of care, as well as each clinical event from the various data sources, are collected and appropriately stored with the correct patient. By collecting all relevant healthcare information for a patient, data analysis is greatly enhanced as compared to traditional approaches. Most pertinent is the ability to compare data from different events that may have come from different sources. For example, the data analysis module 212 could determine how many patients that on taking a particular medication are subsequently treated for a particular condition, for example. By way of another example, the data analysis module 212 could analyze how many patients that have had a given surgical procedure had been given a follow-up laboratory procedure.

In some embodiments, the PHR system 102 may include a filtering module 218. The filtering module 218 may be configured to change modes to vary the resolution of data that is viewed by a user. By "resolution" it is meant that the filtering module 218 may filter the patient data to provide either a higher level view or a lower level view of data in a PHR. For example, consider data in a PHR related to an optic condition. If the filtering module 218 were configured to provide a higher level view, the optic condition may be described merely as "an optic condition." If the filtering module 218 were configured to provide a lower level view, the optic condition may be described as a "staphylococcal eye infection."

In some embodiments, the filtering module 218 may be configured to traverse up and down the SNOMED hierarchy to adjust the resolution of data that is viewed by the user. For example, if the filtering module 218 were configured for the lowest level view, the user may view a description associated with the SNOMED code. If the filtering module 218 were configured for a higher level view, the user may view a description associated with a more generalized code related to the SNOMED code stored in the patient's PHR. For example, if the filtering module 218 were configured for a high level view, and the SNOMED concept related to the SNOMED code in the PHR were "kidney disease," the user may view the more generalized SNOMED concept described as "disorder of the urinary system."

In some embodiments, the filtering module 218 may be configured to filter patient data based on the type of user accessing the information. For example, the filtering module 218 may filter patient data unrelated to the specialty of the physician accessing the PHR database 200. In such an embodiment, physicians may be associated with a specialty code, such as an X12 code, based on the specialty of the physician. A cross-reference table (or other lookup function) may be provided to determine the relevant SNOMED codes based on the specialty code of the physician accessing the patient data. In this manner, the physician will not be overloaded with voluminous patient data, but will be presented with patient data relevant to his/her specialty. Of course, the physician may instruct the filtering module 218 to reveal additional patient data that may not be associated with his/her specialty.

Embodiments are contemplated in which various synonyms may be associated with each medical concept in the PHR. For example, each PHR in the PHR database 200 may include synonyms or synonymous descriptions for one or more entries in the PHR that describe the same medical concept, such as a condition, procedure, etc., using varying terminology. The filtering module 218 may display the synonym that is best suited to the type of user accessing the PHR. Embodiments are contemplated in which certain descriptions may use medical terminology while another description may use layman's terms. For example, a patient accessing his/her PHR may view an entry as "Heart Attack" while a healthcare provider accessing the same entry may view "myocardial infarction." This allows patients to view the PHR using consumer friendly terms whereas health care providers, such as physicians and nurses, can view detailed medical terms.

Figure 10:
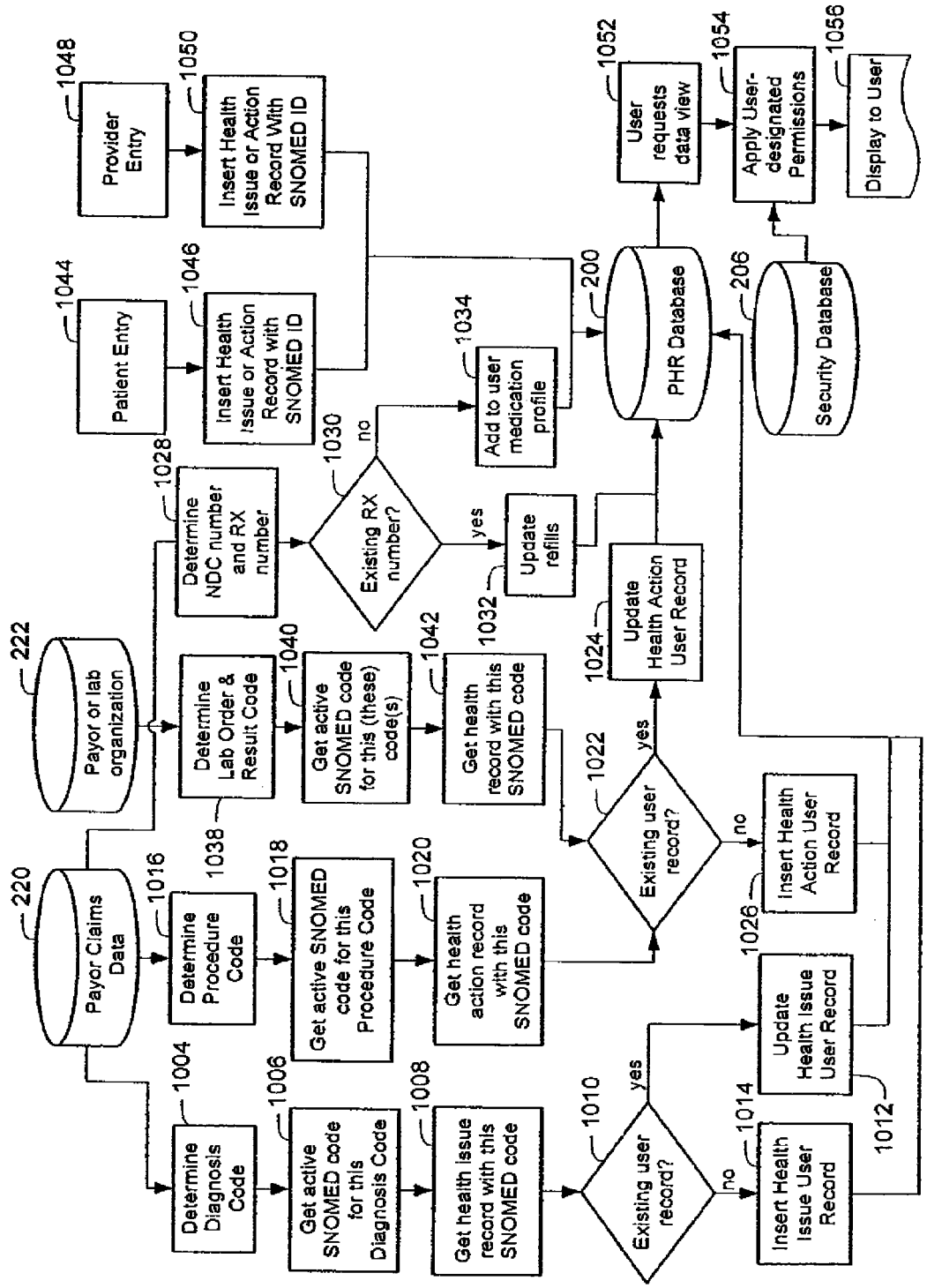
FIG. 10 shows a flow chart which illustrates an embodiment of a system and method for populating a personal/individual health record with data.

FIG. 10 is a diagram showing acts that may be performed by the PHR System 102. In some embodiments, the PHR system 102 may access or be provided with payor claims data 220. In some embodiments, the payor claims data 220 could be comprehensively coded using the SNOMED codes. Using the payor claims data 220, the PHR system 102 may determine, for a selected individual and PHR, the diagnosis code associated with a particular claim. For example, the ICD 9 ("International Classification of Diseases, 91h Revision") code may be determined. This operation is represented by process block 1004. Following this step, the PHR system 102 may retrieve the SNOMED code associated with the diagnosis code. This operation is represented by process block 1006.

Next, as illustrated by process block 1008, a health issue record associated with the SNOMED code may be retrieved. The PHR system 102 may then determine, in decision operation 1010, whether the subject information is already described in an existing user record. If so, the PHR system 102 updates the data, as shown in operation 1012. If not, the PHR system 102 adds this information to the user's PHR, as illustrated by process block 1014. If not, the PHR system 102 populates the user's record with the identified health issue.

In addition to handling diagnosis codes, such as ICD 9 codes, the PHR system may also determine procedure codes, such as CPT ("Current Procedural Terminology") codes, from each unique claim present in the payor claims data 220. (Process Block 1016). As illustrated by process block 1018, the PHR system 102 may retrieve the SNOMED code associated with the subject procedure coded (e.g., CPT code). Following this step, a health action record associated with the subject SNOMED code may be retrieved, as illustrated by process block 1020. The PHR system 102 may then determine, in decision operation 1022, whether the user has this health action as an existing entry. If so, the PHR system 102 updates the data in process block 1024. If not, the PHR system 102 adds this information to the user's PHR, as illustrated by process block 1026.

In some embodiments, the PHR system 102 may be configured to populate a PHR with prescription related information in the payor claims data 220. Process block 1028 represents the operation of determining the NDC ("National Drug Code") number and prescription number for medications identified in the payor claims data. After this information is identified, the PHR system 102 determines, in decision operation 1030, whether the user has this medication or prescription as an existing entry associated with this provider. If yes, refill information is updated, as indicated by process block 1032, as necessary. If no, the PHR system 102 recognizes this information as being new information and adds it to the medication profile in the PHR of the subject user, as indicated by processor block 1034.

In some embodiments, the PHR system 102 may be configured to populate and/or update a PHR using health-related data 222 from an entity (e.g., payor or laboratory organization) other than payor claims data 220. Process block 1038 represents the operation of determining the lab order and/or result code from the health related data 222. As illustrated by process block 1040, the PHR system 102 may retrieve the SNOMED code(s) associated with the code(s). Following this step, a health action record associated with the subject SNOMED code(s) may be retrieved, as illustrated by process block 1042. The PHR system 102 may then determine, in decision operation 1022, whether the user has this health action as an existing entry. If so, the PHR system 102 updates the data in process block 1024. If not, the PHR system 102 adds this information to the user's PHR, as illustrated by process block 1026. In some embodiments, the data from which the SNOMED code is derived (e.g., ICD 9 code, CPT code, NDC code, lab order and/or result code, directly entered data) may be captured for auditing purposes, as this would provide an explanation of the information from which the SNOMED was derived. It should be appreciated that information, other than a SNOMED code, could be derived from the data received from the PHR system 102. For example, the location, type of service, service dates, servicing provider, requesting provided, could also be derived from the payor claims data and/or health related data received from the PHR system 102.

Process block 1044 represents an operation whereby the user can enter information into his or her PHR. This information is preferably entered via an interface that guides the user through the addition of health record entries in such a manner as to capture and classify the appropriate SNOMED code, such as the Connect™ application marketed by the assignee of the present application. Following the entry of this information by the user, the PHR system 102 inserts a corresponding health issue or action into the user's PHR, as illustrated by process block 1046.

Similarly, a health care provider (or other entity) may enter information into the PHR of a selected user, as indicated by process block 1048. This information is also preferably entered via an interface like the Connect™ software. Following entry, a health issue or action is inserted into the provider's PHR, as illustrated by process operation 1050.

Following entry of all health issues or actions by the PHR system 102, as discussed above, the subject issues and actions are stored and tracked in the PHR database 200. One such database is provided as part of the Connect™ application referenced above. An application-specific identifier may be assigned to each member by the Connect™ software.

Process block 1052 illustrates the processing of an access request by a member or user (i.e., one of the individuals for whom a PHR is stored and maintained by the PHR system). A properly logged on and identified user can access the information stored in a PHR stored in PHR database 200. As discussed herein, the PHR system 102 may verify permission of the user as to the requested portion of the PHR, as indicated by process block 1054 and the security database 206. The subject information can be displayed in a variety of formats and using a variety of display to technologies, as illustrated by block 1056.

Although the present disclosure has been described with reference to particular means, materials and embodiments, from the foregoing description, one skilled in the art can easily ascertain the essential characteristics of the invention and various changes and modifications may be made to adapt the various uses and characteristics without departing from the spirit and scope of the invention.

What is claimed is:

1. A computerized method for generating a personal/individual health record, said method comprising a personal health record system server performing the steps:

(a) enrolling a patient in a health plan of a payor, wherein the health plan covers at least a portion of the cost of the patient when a patient undergoes encounters with a plurality of health care providers regarding a health related issue of the patient, wherein under the plan the health care providers request payment for at least a portion of the cost for the encounters from the payor, wherein the plan requires the health care providers to submit health related information of the patient to the payor to support the cost of encounters with the patient;

(b) transferring payor claims data regarding the patient to a personal health record ("PHR") system server;

(c) analyzing, at the PHR system server, said payor claims data concerning the patient to determine which portion of said payor claims data is encounter data comprising one or more of a diagnosis of the patient, a treatment of the patient, a medication of the patient, a procedure of said patient, a history of office visits of the patient with one or more of the health care providers, or duration of office visits of the patient;

(d) populating, at the PHR system server, a personal/individual health record of the patient by storing one or more entries into the personal/individual health record of the patient based on the encounter data, wherein initial population of the personal/individual health record of the patient is based solely on encounter data extracted from the payor claims data;

(e) organizing, at the PHR system server, the personal/individual health record by associating together one or more entries in the personal/individual health record of the patient that are related; and (f) providing a web-based portal accessible by the patient to view the personal/individual health record of the patient.

2. A computerized method for analyzing an electronic health record, said method comprising the steps of:

(a) transferring payor claims data regarding a plurality of patients of a payor to an electronic health record system server, wherein a plurality of patients enrolled in a health plan of the payor undergo encounters with a plurality of health care providers regarding a health related issue of the patients, wherein under the health plan the health care providers request payment for at least a portion of the cost for the encounters from the payor, wherein the health plan requires health care providers to submit health related information of the patients to the payor to support the cost of encounters with the patient;

(b) analyzing at the electronic health record system server said payor claims data concerning a respective patient of the plurality of patients to determine which portion of said payor claims data is encounter data comprising one or more of a diagnosis of the respective patient, a treatment of the respective patient, a medication of the respective patient, a procedure of the respective patient, a history of office visits of the respective patient with one or more of the health care providers, or duration of office visits of the respective patient;

(c) creating at the electronic health record system server electronic health records concerning the plurality of patients by storing one or more entries into the respective patient's electronic health record based on the encounter data, wherein initial population of the electronic health records of the patients is based solely on the encounter data extracted from the payor claims data;

(d) organizing, at the electronic health record system server, the health records by associating together one or more entries in the respective patient's electronic health record that are related; and (e) analyzing the electronic health care records by measuring the outcomes of specific treatments of diseases under investigation and providing a direct comparison of outcomes measured of a specific treatment with various other treatments to allow setting up or modification of clinical protocols.

3. A personal health record ("PHR") system server for use with a patient enrolled in a health plan of a payor, wherein the health plan covers at least a portion of the cost of the patient when a patient undergoes encounters with a plurality of health care providers regarding a health related issue of the patient, wherein under the plan the health care providers request payment for at least a portion of the cost for the encounters from the payor, wherein the plan requires the health care providers to submit health related information of the patient to the payor to support the cost of encounters with the patient, the PHR system server comprising:

a memory for storing instructions and data associated with a personal/individual health record of a patient; and a processor configured to execute the instructions, wherein the instructions cause the processor to perform the steps comprising:

(a) transferring payor claims data of the patient to the ("PHR") system server;

(b) analyzing said payor claims data concerning the patient to determine which portion of said payor claims data is encounter data comprising one or more of a diagnosis of the patient, a treatment of the patient, a medication of the patient, a procedure of said patient, a history of office visits of the patient with one or more of the health care providers, or duration of office visits of the patient;

(c) populating the personal/individual health record of the patient by storing one or more entries into the personal/individual health record of the patient based on the encounter data, wherein initial population of the personal/individual health record of the patient is based solely on encounter data extracted from the payor claims data;

(d) organizing the personal/individual health record by associating together one or more entries in the personal/individual health record of the patient that are related; and (e) providing a web-based portal accessible by the patient to view the personal/individual health record of the patient.

4. An electronic health record system server for use with analyzing electronic health records of a plurality of patients enrolled in a health plan of the payor, wherein the patients undergo encounters with a plurality of health care providers regarding a health related issue of the patients, wherein under the health plan the health care providers request payment for at least a portion of the cost for the encounters from the payor, wherein the health plan requires health care providers to submit health related information of the patients to the payor to support the cost of encounters with the patient, the electronic health record system server comprising:

a memory for storing instructions and data associated with electronic health records of a plurality of patients; and a processor configured to execute the instructions, wherein the instructions cause the processor to perform the steps comprising:

(a) transferring payor claims data regarding the plurality of patients to an electronic health record system server;

(b) analyzing at the electronic health record system server said payor claims data concerning a respective patient of the plurality of patients to determine which portion of said payor claims data is encounter data comprising one or more of a diagnosis of the respective patient, a treatment of the respective patient, a medication of the respective patient, a procedure of the respective patient, a history of office visits of the respective patient with one or more of the health care providers, or duration of office visits of the respective patient;

(c) creating at the electronic health record system server electronic health records concerning the plurality of patients by storing one or more entries into the respective patient's electronic health record based on the encounter data, wherein initial population of the electronic health records of the patients is based solely on the encounter data extracted from the payor claims data;

(d) organizing, at the electronic health record system server, the health records by associating together one or more entries in the respective patient's electronic health record that are related; and (e) analyzing the electronic health care records by measuring the outcomes of specific treatments of diseases under investigation and providing a direct comparison of outcomes measured of a specific treatment with various other treatments to allow setting up or modification of clinical protocols.

5. A personal health record ("PHR") system server for use with a patient enrolled in a health plan of a payor, wherein the health plan covers at least a portion of the cost of the patient when a patient undergoes encounters with a plurality of health care providers regarding a health related issue of the patient, wherein under the plan the health care providers request payment for at least a portion of the cost for the encounters from the payor, wherein the plan requires the health care providers to submit health related information of the patient to the payor to support the cost of encounters with the patient, the PHR system server comprising:

a memory for storing instructions and data associated with a personal/individual health record of the patient; and a processor configured to execute the instructions, wherein the instructions cause the processor to perform the steps comprising:

(a) transferring payor claims data of the patient to the ("PHR") system server;

(b) analyzing said payor claims data to determine which portion of said payor claims data concerning the patient is encounter data comprising one or more of a diagnosis of the patient, a treatment of the patient, a medication of the patient, a procedure of said patient, a history of office visits of the patient with one or more of the health care providers, or duration of office visits of the patient;

(c) populating the personal/individual health record of the patient by storing one or more entries into the personal/individual health record of the patient based on the encounter data, wherein population of at least a portion of the entries in the personal/individual health record of the patient is encounter data extracted from the payor claims data;

(d) organizing the personal/individual health record by associating together one or more entries in the personal/individual health record of the patient that are related; and (e) providing a web-based portal accessible by the patient to view the personal/individual health record of the patient.

6. The method of claim 1, further comprising the step of providing a messaging facility accessible by one or more health care providers of the patient to supplement the personal/individual health record of the patient.

7. The method of claim 2, further comprising the step of providing a messaging facility accessible by one or more health care providers of the patients to supplement the electronic health records of the patients.

8. The method of claim 3, further comprising an instruction for providing a messaging facility accessible by one or more health care providers of the patient to supplement the personal/individual health record of the patient.

9. The method of claim 4, further comprising an instruction for providing a messaging facility accessible by one or more health care providers of the patients to supplement the electronic health records of the patients.

10. The method of claim 5, further comprising an instruction for providing a messaging facility accessible by one or more health care providers of the patient to supplement the personal/individual health record of the patient.

11. The method of claim 1, wherein the web-based portal is configured to allow the patient to supplement the personal/individual health record of the patient.

12. The method of claim 3, wherein the web-based portal is configured to allow the patient to supplement the personal/individual health record of the patient.

13. The method of claim 5, wherein the web-based portal is configured to allow the patient to supplement the personal/individual health record of the patient.

14. The method of claim 1, further comprising the step of providing a messaging facility for supplementing the personal/individual health record of the patient with health related data comprising one or more of laboratory data, imaging data, medication data, or ancillary test data.

15. The method of claim 3, further comprising an instruction for providing a messaging facility for supplementing the personal/individual health record of the patient with health related data comprising one or more of laboratory data, imaging data, medication data, or ancillary test data.

16. The method of claim 5, further comprising an instruction for providing a messaging facility for supplementing the personal/individual health record of the patient with health related data comprising one or more of laboratory data, imaging data, medication data, or ancillary test data.

* * * * *